United States Patent [19]
Jones et al.

[11] Patent Number: 5,366,471
[45] Date of Patent: Nov. 22, 1994

[54] ESOPHAGEAL DILATION BOUGIE

[75] Inventors: Richard G. Jones, West Chester, Pa.; Jeffrey A. Miner, Sanford, Mich.

[73] Assignee: Pilling Co., Fort Washington, Pa.

[21] Appl. No.: 143,446

[22] Filed: Oct. 26, 1993

[51] Int. Cl.⁵ .............................................. A61M 29/00
[52] U.S. Cl. ..................................................... 606/191
[58] Field of Search ................. 606/191; 604/104, 270, 604/170

[56] References Cited

U.S. PATENT DOCUMENTS

| | | | |
|---|---|---|---|
| 4,516,970 | 5/1985 | Kaufman et al. | 604/270 |
| 4,726,373 | 2/1988 | Greengrass. | |
| 4,874,365 | 10/1989 | Frederick et al. | 604/270 |
| 5,017,193 | 5/1991 | Fields | 604/270 |

FOREIGN PATENT DOCUMENTS

WO84/04462 11/1984 WIPO.

OTHER PUBLICATIONS

1993 Pilling Catalog pp. 127 and 543 describing Hurst and Maloney bougies.
Esophageal Dilation: Instruments and Techniques, May 1988, pp. 473–475.

Primary Examiner—Stephen C. Pellegrino
Assistant Examiner—William W. Lewis
Attorney, Agent, or Firm—Howson & Howson

[57] ABSTRACT

An esophageal dilator comprises a hollow, flexible tube filled with a dispersion of Tungsten particles in a fluid silicone material for treating cardiospasm, esophagitis, stenosis and other esophageal diseases.

8 Claims, 1 Drawing Sheet

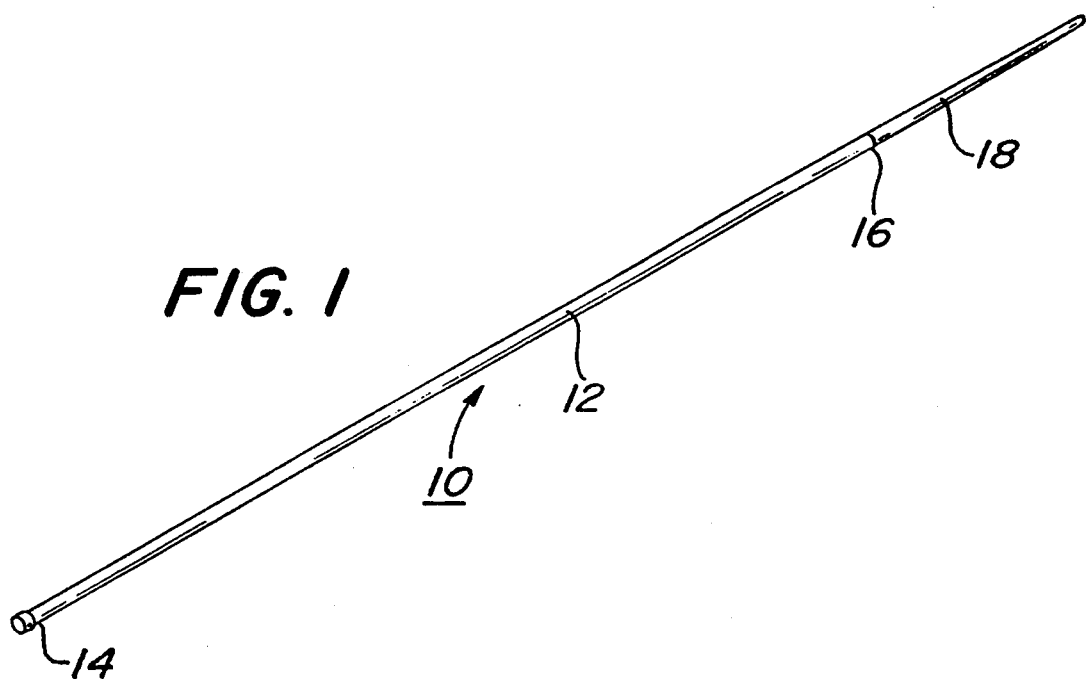
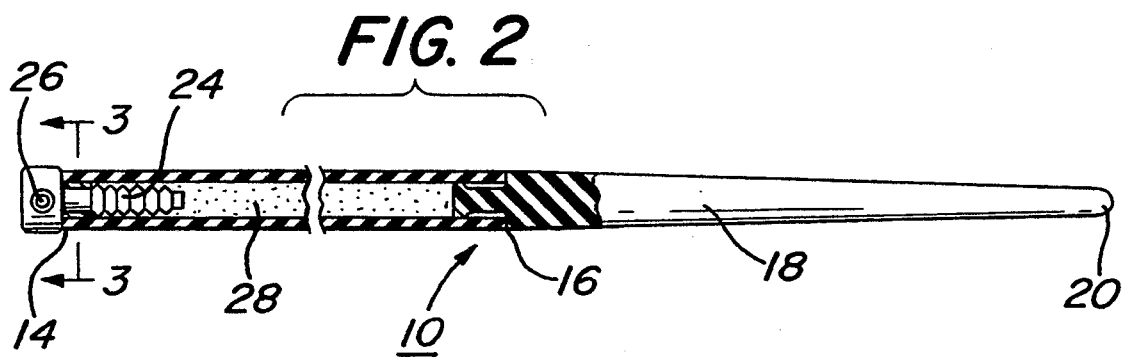
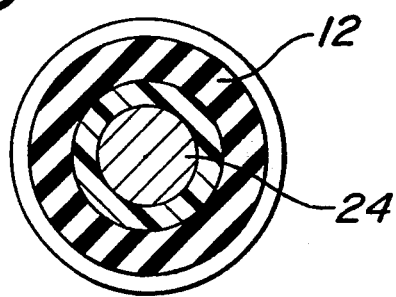

ESOPHAGEAL DILATION BOUGIE

BRIEF SUMMARY OF THE INVENTION

This invention relates to esophageal dilators, and more particularly, to hollow rubber dilators filled with flowable material for treating a constricted esophagus. Stenosis or esophageal stricture, i.e. a narrowing or constricting of the passageway diameter of a patient's esophagus, is associated with several diseases and conditions which affect human beings. Such conditions include, for example, cancer, esophagitis, hernia, cardiospasm, and others associated with the inflammation and/or stricture of the esophagus. For example, cardiospasm is a condition affecting the esophagogastric sphincter, a thick muscular ring between the esophagus and stomach, which is associated with failure of the muscle to relax during swallowing, thus creating an obstruction of the esophageal passageway.

Esophageal strictures prevent the normal peristaltic activities of the esophagus and may impede the patient's ability to swallow and/or block access to the digestive tract. Treatment often requires dilation of the esophagus at its junction with the stomach.

There are several esophageal dilators known in the art. One such dilator is a bougie having a hollow, central channel extending the length of the bougie, for insertion on a guide wire previously placed in the patient. This type of dilator is most often used with tight strictures that are 1.2 centimeters, or less, in diameter. Another type of dilator is a wire-guided balloon dilator. The guide wire locates the balloon in the stricture, and thereafter, the balloon is slowly inflated. The balloon dilator is best used in asymmetrical strictures that are 1.2 centimeters, or more, in diameter.

Another type of esophageal dilator is the Mercury-filled rubber bougie. The bougie comprises a rubber sheath filled with Mercury, and having a tapered tip. The bougie is inserted, tip-first, through a patient's mouth and into the esophagus, applying light pressure to enlarge the diameter of the stricture. The rubber bougie is best used in treating strictures which are symmetrical and more than 1.2 centimeters in diameter. Since most esophageal strictures meet these requirements, the rubber bougie is the most commonly used esophageal dilator.

The Mercury core provides the weight necessary for proper performance of the dilator, and, because Mercury is liquid at ambient and body temperatures, it allows flexing of the dilator.

Ribs can form in the surface of a rubber dilator at the location of a tight bend, and can cause damage to the interior lining of the patient's esophagus. The Mercury core also prevents ribs from forming in the outer surface of the sheath at the location of a tight bend.

One disadvantage to the use of Mercury as the core of a rubber bougie is that Mercury is toxic to humans. The quantity of Mercury held in a bougie could result in a fatality if it were to escape into the patient. The flowability of liquid Mercury enhances the danger, since even a small crack in the sheath of the bougie could result in leakage of the entire quantity of Mercury leaking out of the bougie and into the patient's mouth, esophagus or stomach. If Mercury enters the bloodstream, it can cause mercury poisoning. In addition, the physical action of a large quantity of Mercury on the digestive tract can cause severe effects. Thus, there are significant health risks associated with the use of Mercury.

The principal object of the invention is to provide an esophageal dilation bougie which is similar in performance to a Mercury-filled bougie, but which utilizes a non-toxic flowable material in its core, instead of Mercury. Another object of the invention is to provide a non-toxic bougie which can flex without forming ribs in its outer surface. A further object is to provide a flexible bougie having a core which cannot readily flow out in the event of rupture of the sheath of the bougie. A still further object is to provide a bougie having a flexible core containing Tungsten particles, in which the Tungsten particles are maintained evenly distributed throughout the core.

The esophageal dilation bougie according to this invention comprises a hollow, flexible, tubular sheath having a core of material containing Tungsten particles. The hollow, flexible sheath is preferably made of a silicone rubber, and has a distal end and a proximal end. The distal end is provided with a tapered tip, also preferably of silicone rubber. The portion of the bougie extending proximally from the tapered tip is made radiopaque by virtue of the Tungsten particles in the core. The material is substantially homogeneous and provides the bougie with sufficient weight to effect dilation.

The Tungsten particles are preferably suspended in a fluid silicone material consisting of a mixture of liquid silicone rubber and silicone fluid. Preferably, the mixture consists of approximately 45% by weight liquid silicone rubber and approximately 55% by weight silicone fluid. The Tungsten particles are in the range of 5 to 250 microns in size, and preferably, in the range of 15 to 100 microns. The density of the material is about 9 to about 11 grams per cubic centimeter (g/cc), and preferably, about 9.5 g/cc.

Further objects, features and advantages of the invention will become apparent from the following detailed description when read in conjunction with the drawings.

BRIEF DESCRIPTION OF THE DRAWINGS

FIG. 1 is a perspective view of an esophageal dilation bougie in accordance with the invention;

FIG. 2 is a side elevational of the bougie, partly in axial section, showing the proximal and distal ends of the bougie; and FIG. 3 is a radial section taken on plane 3—3 of FIG. 2.

DETAILED DESCRIPTION

As shown in FIG. 1, the dilation bougie 10 in accordance with the invention comprises an elongated, flexible tube 12, having a proximal end 14 and a distal end 16, and having a tapered tip 18 extending from the distal end. The tapered tip allows the bougie to be inserted into a human patient's mouth, and through the esophagus to the esophagus-stomach junction.

Preferably, the bougie is about 75 cm in overall length, and the tube 18 has a uniform diameter from its distal to its proximal end. The diameter of the bougie is typically in the range of 5.4 mm. to 20 mm. The tip 18 is typically about 15 cm. in length, with a rounded end having a diameter of approximately 4.7 mm and is tapered so that its outer surface smoothly meets the outer surface of tube 12 at distal end 16 of the tube. The tip 18 can be readily introduced through the affected portion of the esophagus, e.g. the cricopharynx area, cardioesophageal junction, or stenosis, so that dilation can be effected.

The tapered tip 18 is provided with an extension 22, which extends into the distal end 16 of tube 12. The tip is secured to the tube by an adhesive, which also seals the distal opening of the tube. A plug 24 is inserted into the opening at the proximal end of tube 12 and is bonded in place. The plug has a transverse hole 26 for a wrist cord.

The tapered tip 18 and the plug 24 seal a hollow space inside the tube 18. This hollow space is filled with a material 28, which, in accordance with the invention, comprises Tungsten particles, preferably suspended in a fluid silicone.

Tube 12 must be flexible to follow the passageway through the mouth and esophagus. Any silicone composition, particularly silicone rubber which passes USP Class IV testing, and which exhibits sufficient strength to encapsulate flowable material 28, and resist rupture during extended use, may be used. Tapered tip 18 and plug 24 are also made of silicone rubber.

Tungsten is a desirable material for use in the core of the tube for several reasons. It can be provided in powdered form; it is non-toxic to humans; and it is radiopaque.

Generally, the useful range of particle sizes for Tungsten powder in the bougie is about 5 to 250 microns, referring to the maximum dimension of the Tungsten particle. However, particles in the range of about 15 to about 100 microns provide the bougie with the best flexure and weight characteristics, and are preferred. The Tungsten powder allows the bougie to be bent in a tight radius and prevents ribs from forming on the outer surface of the bougie.

The radiopaque character of the Tungsten particles makes it possible to observe the bougie by fluoroscopy, and to monitor the location of the bougie relative to the esophageal stricture being treated.

Although the Tungsten is not as dense as Mercury, its density is sufficient to provide the weight necessary for proper performance of the esophageal bougie, even when the tungsten is in the form of particles suspended in a dispersion medium.

Although it is possible to use tungsten particles by themselves as the core of the bougie, in accordance with the invention, the particles are preferably suspended in a dispersion medium. The dispersion medium is desirably a fluid material which causes the Tungsten to remain evenly distributed throughout the space within the interior of tube 12. The dispersion medium prevents clumping of the Tungsten powder and provides the bougie with a uniform flexibility along its length.

One suitable dispersion medium according to the invention is a fluid silicone material. The preferred medium consists of a mixture of about 40% to about 50% by weight liquid silicone rubber and about 50% to about 60% by weight silicone fluid. As used herein, "liquid silicone rubber" is a material having the consistency of a paste. Chemically, it is similar to the casing material, methyl vinyl siloxane. The currently preferred silicone liquid rubber is Wacker LR-15. As used herein, "silicone fluid" is a methyl vinyl material without the vinyl terminations on the methyl vinyl siloxane chains associated with liquid silicone rubbers. The currently preferred silicone fluid is Wacker 101-100. Currently, the preferred dispersion medium consists of about 45% by weight liquid silicone rubber and about 55% silicone fluid. This silicone mixture provides the material encapsulated within the bougie with sufficient flexibility, while providing it with sufficient stiffness to prevent rapid leakage in the event of a rupture of the sheath of the bougie.

Since the density of the dispersion medium is lower than that of the Tungsten, the weight of the mixture of Tungsten and dispersion medium, and thus the weight of the bougie, can be altered by adjusting the ratio of Tungsten to dispersion medium. The ratio can vary from about 1:0 (100% Tungsten) to about 24:1 Tungsten to silicone mixture, by weight. Currently, the preferred ratio of Tungsten to the silicone mixture described above is about 14:1, by weight, giving the material a density of approximately 9.5 g/cc.

Various other modifications can be made to the bougie as described. For example, while a dispersion medium consisting of about 45% by weight liquid silicone rubber and about 55% silicone fluid is preferred, various silicone gels and other mixtures and materials can be used to suspend the tungsten particles.

Still other modifications can be made to the esophageal dilation bougie described above without departing from the scope of the invention as defined in the following claims.

We claim:

1. An esophageal dilation bougie for treating esophageal strictures comprising a flexible tube of silicone rubber having a distal end and a proximal end, with a tapered tip at the distal end and having an enclosed, hollow space extending proximally from the tapered tip, the hollow space being filled with a substantially homogeneous material; wherein a portion of the bougie extending proximally from the tip is radiopaque and sufficiently heavy to effect dilation, and in which the material comprises Tungsten particles suspended in a fluid silicone material.

2. An esophageal dilation bougie according to claim 1 in which substantially all of the Tungsten particles are in the range of 5 to 250 microns in size.

3. An esophageal dilation bougie according to claim 1 in which substantially all of the Tungsten particles are in the range of 15 to 100 microns in size.

4. An esophageal dilation bougie according to claim 1 in which the Tungsten particles are present in the material in an amount such that the density of the flowable material is approximately 9 to 11 g/cc.

5. An esophageal dilation bougie according to claim 1 in which the Tungsten particles are present in the material in an amount such that the density of the material is approximately 9.5 g/cc.

6. An esophageal dilation bougie for treating esophageal strictures comprising a flexible tube of silicone rubber having a distal end and a proximal end, with a tapered tip at the distal end and having an enclosed, hollow spaced extending proximally from the tapered tip, the hollow space being filled with a substantially homogeneous material; wherein a portion of the bougie extending proximally from the tip is radiopaque and sufficiently heavy to effect dilation, and in which the material comprises Tungsten particles suspended in a mixture of liquid silicone rubber and silicone fluid.

7. An esophageal dilation bougie according to claim 6 in which the mixture of liquid silicone rubber and silicone fluid consists of approximately 40% to 50% by weight liquid silicone rubber and approximately 50% to 60% by weight silicone fluid.

8. An esophageal dilation bougie according to claim 6 in which the mixture of liquid silicone rubber and silicone fluid consists of approximately 45% by weight liquid silicone rubber and approximately 55% by weight silicone fluid.

* * * * *